US006224541B1

(12) United States Patent
Thompson

(10) Patent No.: US 6,224,541 B1
(45) Date of Patent: May 1, 2001

(54) MEDICATION DELIVERING CLITORAL STIMULATION DEVICE

(75) Inventor: Ronald J. Thompson, Fort Thomas, KY (US)

(73) Assignee: 40 J's LLC

( * ) Notice: Subject to any disclaimer, the term of this patent is extended or adjusted under 35 U.S.C. 154(b) by 0 days.

(21) Appl. No.: 09/414,250

(22) Filed: Oct. 7, 1999

Related U.S. Application Data

(63) Continuation-in-part of application No. 09/340,227, filed on Jul. 1, 1999.

(51) Int. Cl.$^7$ .............................. A61F 5/00
(52) U.S. Cl. .............................. 600/38
(58) Field of Search .............................. 600/38, 29; 601/84

(56) References Cited

U.S. PATENT DOCUMENTS

| | | | | |
|---|---|---|---|---|
| 4,139,006 | * | 2/1979 | Corey | 600/29 |
| 5,386,836 | * | 2/1995 | Biswas | 600/29 |
| 5,460,597 | * | 10/1995 | Hopper | 601/84 |

* cited by examiner

*Primary Examiner*—Cary O'Connor
*Assistant Examiner*—Brian Szmal
(74) *Attorney, Agent, or Firm*—Don Halgren

(57) ABSTRACT

The present invention involves a clitoral stimulation apparatus for the holding and timed distribution of a gel or cream onto the clitoris of a user of the apparatus. The apparatus comprises an enclosing body having a first end and a second end, a channel-shaped clitoris-interfacing surface on the first end of the body, and a gel or cream distribution arrangement on the body of the apparatus to permit the user to be clitorally stimulated as desired.

20 Claims, 2 Drawing Sheets

MEDICATION DELIVERING CLITORAL STIMULATION DEVICE

This application is a continuation-in-part of copending application(s) application Ser. No. 09/340,227 filed on Jul. 1, 1999.

BACKGROUND OF THE INVENTION

1. Field of the Invention

This invention relates to arrangements for clitoral stimulation, and more particularly to a device for delivering medicaments to the clitoris for a stimulation thereof, and is a continuation-in-part application of my co-pending U.S. application Ser. No. 09/340,227, filed Jul. 1, 1999, and incorporated herein by reference, in its entirety.

2. Prior Art

Addressing womens' sexuality concerns is no longer taboo. Since the recent introduction and success of Viagra therapy for men, womens' concerns are finally being addressed. The characteristics of the female anatomy require that such stimulating products be in the form of a cream or a gel.

In the human anatomy, and more particularly in the female anatomy, there are two types of integument (skin): keratinized stratified squamous epithelium, and non-keratinized stratified squamous epithelium, more commonly referred to as mucous membrane. The entire external surface of the body is covered with keratinized stratified squamous epithelium except the lips, mouth, anus, and the vagina/vulva in females. If a lotion is applied to the keratinized squamous epithelium, it is absorbed only by the top layers of the skin. Multiple transdermal medications are delivered through the keratinized skin, but the delivery system is very sophisticated. Absorption of medications is much easier if they are delivered to mucous membranes, or non-keratinized stratified squamous epithelium, especially the vulva and vaginal mucosa. Many vaginal creams, and suppositories that dissolve to become creams with the moisture and heat of the vagina, have been sold for over fifty years. All of the vaginal creams and suppositories are absorbed into the full thickness of the non-keratinized stratified squamous epithelium that defines the vaginal mucosa. Some of the vaginal creams are systemically absorbed by the blood vessels in the basement membrane of the vaginal mucosa, while other medications are not systemically absorbed. Systemic absorption refers to the distribution of the medication throughout all tissues of the body via the blood stream. The vaginal/vulvac mucosa is a multiple layer of non-keratinized stratified squamous epithelial cells twenty-to-thirty cells in thickness from the basement membrane to the outermost cells of the mucosa. Antifingal creams are absorbed by the vaginal mucosa, where they act to kill monilia, but are not systemically absorbed. Some estrogen creams are systemically absorbed and others are not, but both types have a local growth effect on the vaginal mucosa and are absorbed by the full thickness of the mucosa and even the dermis that supports the epidermis (the vaginal mucosa).

Currently, a number of medicated creams are being developed to enable, or to enhance female sexual stimulation and response by direct actions on the clitoris. All of these creams are intended to be topically applied directly to the vulvae and clitoris. The top of the clitoris is covered by the clitoral hood, an extension of the labia minora; any medication applied to the clitoral hood is poorly absorbed because this tissue is partially keratinized stratified squamous epithelium. The under-carriage of the clitoris is a mucous membrane-non-keratinized epithelium—and a medication applied to the undercarriage of the clitoris is well absorbed. The absorption of the medication by the mucous membrane of the clitoris will diffuse into the entire clitoris and be effective. However, the application of a medicated cream specifically to the undercarriage of the clitoris is not only a difficult maneuver because it is done blindly, by feel only; it is also an ineffectual one, because medication placed on the clitoral hood or labia minora will be relatively futile. The misapplication of the medication might lead women to believe the medication is ineffective, when, in reality, it was simply misplaced. In addition, clitoral application might not be well accepted by a number of women because of their unfamiliarity with the vulvar anatomy. Some women might not only be reluctant to attempt to apply a cream directly to the under-carriage of the clitoris, but might also choose not to use the medication cream because of embarrassment.

The anatomy of the clitoris and the physiological action of the vasoactive creams for stimulation thereof is generally similar to the anatomy of males. The clitoral artery, located in the middle of the clitoris and extending lengthwise from the base to the tip of the clitoris, supplies blood to the clitoris. Two clitoral veins, located on either side of the clitoral artery, normally drain the clitoris of the blood pumped into it from the artery. As female sexual arousal initiates, either by direct stimulation of the clitoris or by the application of one of the recently developed female arousal creams, valves of the clitoral veins located at the base of the clitoris close, and the venous blood fills two honeycomb-like chambers, the cavernous cavernosa. The corpus cavernosa are normally empty of blood, but, like the clitoral artery and veins, they are positioned lengthwise from the base to the tip of the clitoris. Therefore, as the valves in the veins at the base of the clitoris close, the blood pumped into the clitoris artery distends the corpus cavernosa. This causes the clitoris to enlarge two-to-three fold, and to become erect, rigid, and highly sensitive, just as the penis in the male. In fact, the penis and the clitoris are the exact same structures. Female clitoral enlargement and rigidity and male penile erection are both accomplished by the same action: closure of the venous valves located at the base of each structure. Drugs (like Viagra) that cause closure of these venous valves are classified as vasoactive drugs. Several development programs by major drug companies are currently attempting to produce Viagra-like vasoactive creams to apply to the clitoris to enhance female sexual response.

BRIEF SUMMARY OF THE INVENTION

The primary function of the present invention is the specific placement of a medication so that it directly interfaces with non-keratinized stratified squamous mucous membrane located on the ventral aspect, or under-carriage, of the clitoris. This exact positioning would be accomplished by use of an adhesive-backed device described in my patent application Ser. No. 09/340,227. The present invention addresses the need for applying and properly positioning a cream or gel-like medication, scented or unscented, flavored or unflavored, against the mucous membrane particularly where the moisture of the tissue causes the medication to dissolve, and because of the lack of keratin, encourages local tissue absorption of that medication. The body heat of 37 degrees centigrade, combined with the mucous membrane serum transudate moisture, acts to dissolve the physiological active ingredients of the medicated cream, and allows the diffusion of the dissolved active ingredient into the clitoral tissue. The absorbed vasoactive cream can then effect the drug-mediated arousal and increased sensitivity of the clitoris.

Three types of drug delivery arrangements and stimulator embodiments could be utilized by the adhesive-backed clitoral stimulating device. They are a semi-solid molded cap attached to the clitoral interfacing surface of the device, a cream applied to the clitoral interfacing surface just before the actual use of the device, and a reservoir to hold the cream located within the body of the device with a communicating channel to the surface interfacing with the clitoris.

The first embodiment comprises a unique cap design medication applicator. Medicated suppositories are actually a suspension of the active medication within a cocoa butter matrix. The semisolid suppository is inserted into the vagina and dissolves because of the heat and transudate moisture of the vagina. The active ingredient is thus absorbed by the non-keratinized stratified squamous epithelium-the vaginal mucosa. The cap design would actually be preformed, and, by the use of a compatible adhesive, attached to the clitoral interfacing surface of the clitoral stimulating device. Once placed and held in place by the adhesive backing of the clitoral stimulating device, the cocoa butter matrix would dissolve and the active medication would be absorbed by the undercarriage of the clitoris.

The second embodiment of the present invention would be an increased surface area on the superior aspect of the medication applicator clitoral stimulating device intended to be positioned against the clitoris. The user would apply a medicated cream directly to the top aspect of the device as a person applies toothpaste to a toothbrush before use. When the device is loaded with medicated cream, it is positioned against the clitoris, and the medicated cream is in direct contact with the non-keratinized stratified squamous eqithelium (the mucous membrane) of the undercarriage of the clitoris.

A third embodiment of the present invention would be a pre-loaded reservoir located within the body of the resilient silicone, clitoral-stimulating medicament applicator. The reservoir would contain a channel for the delivery of the medicated cream from the reservoir to the surface interfacing the clitoris. This reservoir would be pre-loaded with a medicated cream, having a distribution channel covered by an adhesive-backed release paper. The user removes the release paper, the medication would cover the surface of the device interfacing with the undercarriage of the clitoris. A pinching force applied to the sides of the applicator as it is placed under the clitoris would squeeze the medicated cream out of the reservoir and apply the cream directly to the clitoris. The pressure exerted on the device from intercourse would also cause continuous release of the medication from the reservoir to the clitoris over a period of time. The reservoir would be constructed with a thin wall, and, due to the elastic properties of the silicone, the reservoir would collapse as it is depleted of medicated cream. The reservoir could be filled with a suppository-like cocoa butter medication as in the cap design of the first embodiment. The medication would be solid or semi-solid at room temperature, but would liquefy at body temperature to allow the medication to exit the reservoir and be applied directly to the undercarriage of the clitoris by the top surface of the device.

A further embodiment of the present invention includes a battery powered vibratory generator arranged within the body of the applicator. A pressure, heat or moisture sensitive switch or release may be arranged on a side portion of the applicator to activate the vibratory generator created motion within the applicator before or as it is applied against the clitoris. The vibratory motion of the stimulator has the dual effect of stimulating the clitoris by stimulator motion itself, as well as the effect of pumping or distributing out any cream of gel on or in the stimulator.

The invention thus comprises a clitoral stimulation apparatus for the holding and timed distribution of a gel or cream onto the clitoris of a user of said apparatus, comprising: an enclosing body having a first end and a second end; a channel-shaped clitoris-interfacing surface on the first end; and a gel or cream distribution arrangement on the body of the apparatus. The enclosing body is of generally triangular shape having said first end truncated. The gel or cream distribution arrangement includes a gel or cream reservoir arranged within the body of the apparatus. The distribution arrangement may include a conduit from the reservoir to the tissue interfacing surface. The distribution arrangement may include a roughened texture on the channel-shaped clitoral-interfacing surface. The clitoral stimulation apparatus may include a pair of sloped side walls defining the body of the apparatus, against which the vaginal labora minor will rest. A tab may be arranged on the body between the side walls, for gripping and manipulating the apparatus by a user thereof, interfacing surface may have a cap of medicament adhesively attached thereon. The interfacing surface may have an adhesively backed release sheet thereon, to permit discharge of cream or gel through the conduit from the reservoir to the interfacing surface when the release sheet is removed. A vibratory generator may be arranged within the body of the apparatus. The vibratory generator may be activated by a pressure sensitive switch on the body of the apparatus. The vibratory generator may be activated by a heat sensitive switch on the body of the apparatus. The vibratory generator may also activated by a moisture sensitive release on the body of the apparatus. The enclosing body may have a lowermost surface with a tissue adhering adhesive thereon for securement of the apparatus to a user of the apparatus.

The invention also includes a method of stimulating a clitoral organ of a user by the application of a clitoral tissue stimulating medicament to the clitoral tissue, comprising the steps of: providing a clitoral interfacing apparatus with a clitoral interfacing surface; applying a clitoral stimulating medicament onto the clitoral interfacing surface; and placing the apparatus against the user's clitoris to permit the medicament to engage and effect the clitoris. The steps include arranging a medicament holding reservoir within the apparatus; and connecting the reservoir and the interfacing surface by a conduit; placing a vibratory generator within the apparatus to permit a vibratory motion to be switched on in the apparatus, on by the user.

BRIEF DESCRIPTION OF THE DRAWINGS

The objects and advantages of the present invention will become more apparent when viewed with the following drawings, in which.

DESCRIPTION OF THE PREFERRED EMBODIMENTS

Figure 1:
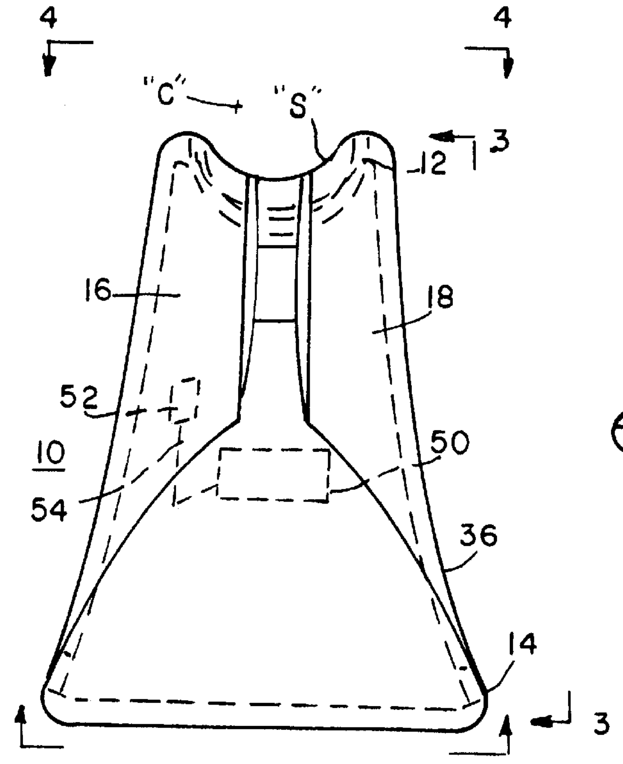
FIG. 1 is a plan view of a clitoral stimulation applicator of the present invention.
Figure 2:
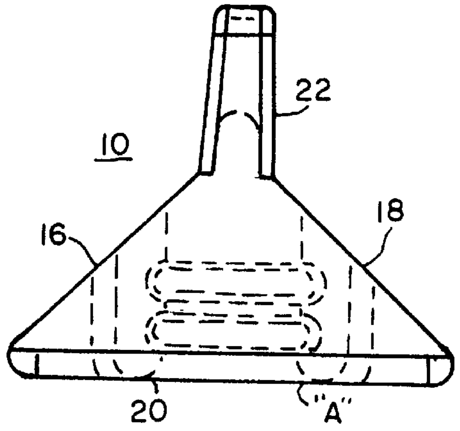
FIG. 2 is a view taken along the lines 2—2 of FIG. 1.
Figure 3:
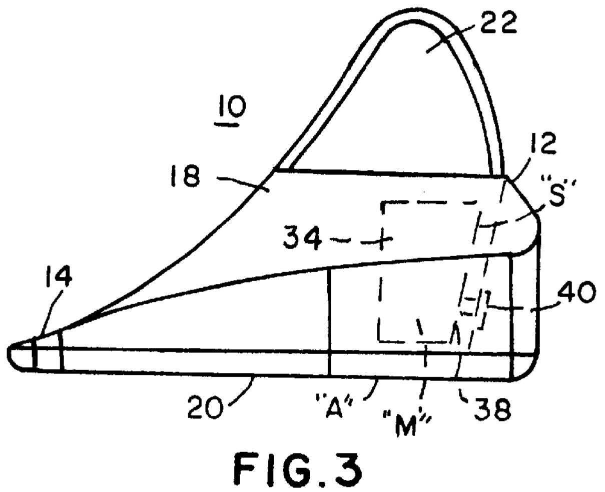
FIG. 3 is a view taken along the lines 3—3 of FIG. 1.
Figure 4:
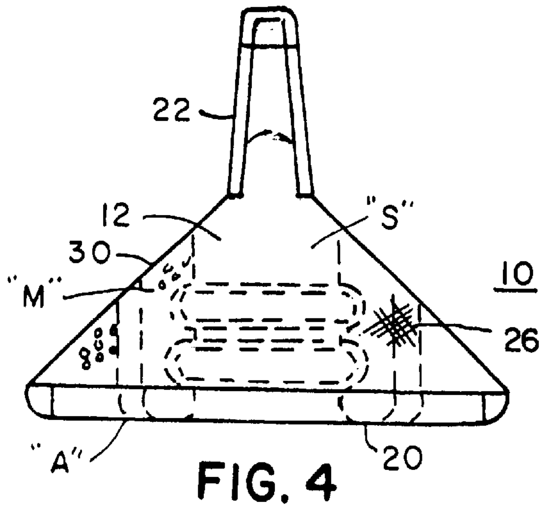
FIG. 4 is a view taken along the lines 4—4 of FIG. 1.
Figure 5:
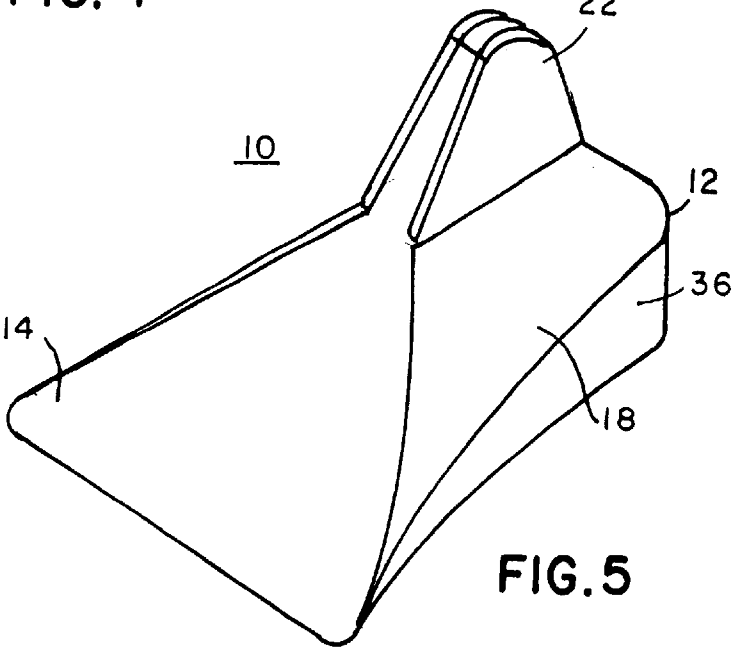
FIG. 5 is a perspective view of the clitoral stimulation applicator shown in FIG. 1.

Referring now to the drawings in detail, and particularly to FIG. 1, there is shown the present invention comprises a clitoral stimulating medication applicator 10 preferably made from a silicon having a shaped somewhat in a triangular configuration having a truncated first end 12, and a broadened second end 14, as may be seen in FIG. 1. The first end 12 is channel shaped so as to provide a conforming notch-like surface "S" to engage with the interfacing surface of a clitoris "C". The stimulating applicator 10 has sloped side walls 16 and 18 arranged to be covered by the labia minor. The stimulator applicator 10 has a planar lower surface 20, as shown in FIGS. 2, 3 and 4. The lower surface 20 is preferably covered with a mild adhesive "A" for securement to the stimulator applicator "user", which securement arrangement is identified in my aforementioned co-pending U.S. Patent Application. A tab 22 is molded into the ridge line between the two sloped side walls 16 and 18. The first end 12 of the applicator 10 in a first preferred embodiment has a layer or cap 26 of a medicated suppository thereon. Such medicated suppositories are actually a suspension of an active medication within a cocoa butter matrix and dissolves when placed against the clitoris because of the heat and transudate moisture of the vagina. The active ingredient is thus absorbed by the non-keratinized stratified squamous epithelium-the vaginal mucosa. The cap 26 may be made as a medicated suppository which is actually a suspension of an active medication within a cocoa butter matrix. The semisolid suppository is inserted into the vagina and dissolves because of the heat and transudate moisture of the vagina. The active ingredient is thus absorbed by the non-keratinized stratified squamous epithelium-the vaginal mucosa. The cap 26 may be actually be preformed, and, by the use of a compatible adhesive, attached to the clitoral interfacing surface "S" of the clitoral stimulation applicator 10. Once placed and held in place by the adhesive backing of the clitoral stimulating device, the cocoa butter matrix would dissolve and the active medication would be absorbed by the undercarriage of the clitoris.

The second embodiment of the clitoral stimulation medication applicator 10 includes a surface "S" having depressions or a roughened surface 30, which would entrap and hold a medicated cream directly to the top aspect of the device as a person applies toothpaste to a toothbrush before use. When the device is loaded with a medicated cream "M", it is positioned against the clitoris, and the medicated cream is in direct contact with the non-keratinized stratified squamous eqithelium (the mucous membrane) of the undercarriage of the clitoris.

Another preferred embodiment of the clitoral stimulator 10 is a pre-loaded reservoir 34 located within the body 36 of the resilient silicone, clitoral-stimulating medicament applicator. The reservoir 34 would contain at least one channel 38 for the delivery of the medicated cream "M" from the reservoir 34 to the surface "S" interfacing the clitoris. This reservoir 34 would be pre-loaded with a medicated cream "M", having its distribution channel(s) 38 covered by an adhesive-backed release paper 40. The user removes the release paper 40, and the medication "M" would then cover the surface "S" of the applicator 10 interfacing with the undercarriage of the clitoris. A pinching force applied to the soft sidewalls 16 and 18 of the applicator 10 as it is placed under the clitoris would squeeze the medicated cream "M" out of the reservoir 34 and apply the cream directly to the clitoris. The pressure exerted on the device from intercourse would also cause continuous release of the medication from the reservoir 34 to the clitoris over a period of time. The reservoir 34 would be constructed with a thin wall, and, due to the elastic properties of the silicone, the reservoir 34 would collapse as it is depleted of medicated cream. The reservoir could be filled with a suppository-like cocoa butter medication as in the layered cap 26 of the first embodiment. The medication "M" may be solid or semi-solid at room temperature, but would liquefy at body temperature to allow the medication to exit the reservoir 34 and be applied directly to the undercarriage of the clitoris by the interfacing surface "S" of the device.

A further embodiment of the present clitoral stimulator 10 includes a battery powered vibratory generator 50 arranged within the body 36 of the applicator 10 as indicated in FIG. 1. A pressure, heat or moisture sensitive switch or release 52 may be arranged on a side portion of the applicator 10, and communicating through a proper circuit 54, to activate the vibratory generator created motion within the applicator 10 before or as it is applied against the clitoris. The vibratory motion of the stimulation applicator 10 has the dual effect of stimulating the clitoris by stimulator motion itself, as well as the effect of pumping or distributing out any cream of gel on the surface "S" or in the reservoir 34 of the stimulation applicator 10.

Figure 6:
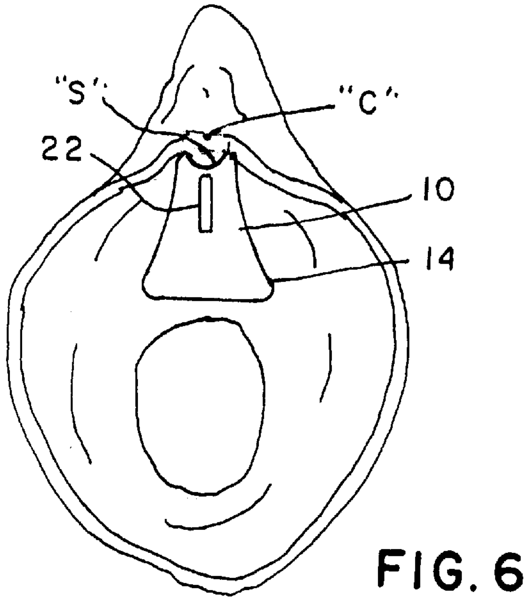
FIG. 6 is a representation of the applicator arranged in position against a clitoris.

FIG. 6 represents the emplacement of a stimulation applicator 10 against a clitoris "C" on a user of such device.

Thus there has been shown a unique clitoral stimulation apparatus for holding/supporting and distributing a stimulatory gel, cream or medicament to the clitoris of a user of such apparatus. Such apparatus includes vibratory means to facilitate stimulation of the clitoris and for the timed application of medicament to the clitoris as well.

I claim:

1. A clitoral stimulation apparatus for the holding and timed distribution of a gel or cream onto the clitoris of a user of said apparatus, comprising:

an enclosing body having a first end and a second end;

a channel-shaped clitoris-interfacing surface on said first end; and a gel or cream distribution arrangement on said body of said apparatus.

2. The clitoral stimulation apparatus as recited in claim 1, wherein said enclosing body is of generally triangular shape having said first end truncated.

3. The clitoral stimulation apparatus as recited in claim 1, wherein said gel or cream distribution arrangement includes a gel or cream reservoir arranged within said body of said apparatus.

4. The clitoral stimulation apparatus as recited in claim 3, wherein said distribution arrangement includes a conduit from said reservoir to said tissue interfacing surface.

5. The clitoral stimulation apparatus as recited in claim 1, wherein said distribution arrangement includes a roughened texture on said channel-shaped clitoral-interfacing surface.

6. The clitoral stimulation apparatus as recited in claim 1, including a pair of sloped side walls defining said body of said apparatus, against which the vaginal labora minor will rest.

7. The clitoral stimulation apparatus as recited in claim 6, including a tab arranged on said body between said sidewalls for gripping and manipulating said apparatus by a user thereof.

8. The clitoral apparatus as recited in claim 1, wherein said interfacing surface has a cap of medicament adhesively attached thereon.

9. The clitoral apparatus as recited in claim 4, wherein said interfacing surface has an adhesively backed release sheet thereon, to permit discharge of cream or gel through said conduit from said reservoir to said interfacing surface when said release sheet is removed.

10. The clitoral stimulation apparatus as recited in claim 1, including a vibratory generator arranged within said body of said apparatus.

11. The clitoral stimulation apparatus as recited in claim 10, wherein said vibratory generator is activated by a pressure sensitive switch on said body.

12. The clitoral stimulation apparatus as recited in claim 10, wherein said vibratory generator is activated by a heat sensitive switch on said body.

13. The clitoral stimulation apparatus as recited in claim 10, wherein said vibratory generator is activated by a moisture sensitive release on said body.

14. The clitoral stimulation apparatus as recited in claim 1, wherein said enclosing body has a lowermost surface, said lowermost surface having a tissue adhering adhesive thereon for securement of said apparatus to a user of said apparatus.

15. A method of stimulating a clitoral organ of a user by the application of a clitoral tissue stimulating medicament to said clitoral tissue, comprising the steps of:

providing a clitoral interfacing apparatus with a clitoral interfacing surface;

applying a clitoral stimulating medicament onto said clitoral interfacing surface; and placing said apparatus against said user's clitoris to permit said medicament to engage and effect said clitoris.

16. The method of stimulating a clitoral organ of a user by a clitoral tissue stimulating apparatus, as recited in claim 15, including the step of:

arranging a medicament holding reservoir within said apparatus; and connecting said reservoir and said interfacing surface by a conduit.

17. The method of stimulating a clitoral organ of a user by a clitoral tissue stimulating apparatus as recited in claim 15, including the step of:

placing a vibratory generator within said apparatus to permit a vibratory motion to be switched on in said apparatus, on by said user.

18. The method of stimulating a clitoral organ of a user by a clitoral tissue stimulating apparatus as recited in claim 15, including the step of:

attaching said medicament to said apparatus by an adhesive therebetween.

19. The method of stimulating a clitoral organ of a user by a clitoral tissue stimulating apparatus as recited in claim 15, including the step of:

roughenig said interfacing surface of said apparatus.

20. The method of stimulating a clitoral organ of a user by a clitoral tissue stimulating apparatus as recited in claim 17, including the step of:

arranging an sensor on said apparatus to activate said vibratory generator in said apparatus.

* * * * *